(12) United States Patent
Krogh et al.

(10) Patent No.: US 8,888,743 B2
(45) Date of Patent: Nov. 18, 2014

(54) BATTERY MANAGEMENT SYSTEM

(75) Inventors: Ross G. Krogh, Long Grove, IL (US); James P. Martucci, Libertyville, IL (US); Jeffrey D. Kotecki, Vernon Hills, IL (US); Miroslaw Grzeszykowski, Deland, FL (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 132 days.

(21) Appl. No.: 13/316,973

(22) Filed: Dec. 12, 2011

(65) Prior Publication Data
US 2012/0150114 A1   Jun. 14, 2012

Related U.S. Application Data
(60) Provisional application No. 61/422,524, filed on Dec. 13, 2010.

(51) Int. Cl.
| | |
|---|---|
| A61M 1/00 | (2006.01) |
| H02J 7/00 | (2006.01) |
| G01N 27/42 | (2006.01) |
| A61M 5/142 | (2006.01) |
| G01R 31/36 | (2006.01) |
| H02J 9/06 | (2006.01) |

(52) U.S. Cl.
CPC ....... *A61M 5/142* (2013.01); *A61M 2205/8256* (2013.01); *A61M 2205/8206* (2013.01); *G01R 31/36* (2013.01); *H02J 7/008* (2013.01); *H02J 7/0021* (2013.01); *H02J 9/06* (2013.01)
USPC ............ 604/151; 320/121; 320/136; 324/425

(58) Field of Classification Search
USPC ............... 604/65–67, 131–151; 340/636.1, 340/636.15; 324/426, 434, 425; 320/155, 320/156, 125, DIG. 21, 121, 135, 136
See application file for complete search history.

(56) References Cited

U.S. PATENT DOCUMENTS

| | | | | |
|---|---|---|---|---|
| 4,698,578 A | * | 10/1987 | Mullersman et al. | ......... 320/121 |
| 5,712,795 A | * | 1/1998 | Layman et al. | ................ 700/297 |

(Continued)

FOREIGN PATENT DOCUMENTS

| | | |
|---|---|---|
| EP | 0546569 | 6/1993 |
| EP | 0792001 | 8/1997 |
| WO | WO 97/13310 | 4/1997 |

OTHER PUBLICATIONS

International Search Report and Written Opinion for corresponding International Application No. PCT/US2011/064374 (Jun. 15, 2012).

*Primary Examiner* — Matthew F DeSanto
(74) *Attorney, Agent, or Firm* — Marshall, Gerstein & Borun LLP

(57) ABSTRACT

A battery management system is provided for one or more batteries. The system includes a display unit, and a controller coupled to the display unit and programmed to determine when a healthcare delivery system is coupled to the one or more batteries, to control the display unit to display an initial number corresponding to a time remaining on battery (TROB) when the healthcare delivery system is coupled to the one or more batteries, to determine if the TROB is within a reserve range extending up to a reserve range maximum, the reserve range maximum being less than a maximum TROB, to change the TROB according to an operational state of the healthcare delivery system if the TROB is greater than the reserve range maximum, and to decrease the TROB without regard for the operational state of the healthcare delivery system if the TROB is less than the reserve range maximum.

24 Claims, 3 Drawing Sheets

(56) References Cited

U.S. PATENT DOCUMENTS

| | | | | |
|---|---|---|---|---|
| 5,764,034 | A | * | 6/1998 | Bowman et al. ............. 320/155 |
| 6,157,169 | A | * | 12/2000 | Lee ............................. 320/132 |
| 6,348,777 | B1 | | 2/2002 | Brown et al. |
| 7,132,832 | B2 | * | 11/2006 | Vaillancourt et al. ......... 324/426 |
| 2010/0198537 | A1 | | 8/2010 | Takemori |

* cited by examiner

BATTERY MANAGEMENT SYSTEM

BACKGROUND

This patent is directed to a battery management system, and, in particular, to a battery management system for use with a healthcare delivery system, such as a healthcare delivery system including an infusion pump and pump controller.

Therapy, or treatment, for a medical condition may be characterized in a number of different ways. For example, therapy may be discussed in terms of the agent used to affect a change in the patient's condition, such as a drug or radiation. As another example, therapy may be discussed in terms of the mode or route of administration.

Infusion therapy—the intravenous delivery (i.e., delivery into a vein) of therapy—is well known in the art. In its simplest form, infusion therapy may be carried out using a container or bag connected to a patient via a drip chamber, an administration set and a catheter. In such a system and according to such a method, fluid passes from the bag to the patient under the influence of gravity. In a more complex system, a pump or a cuff may be used to control the flow of the fluid to the patient.

When a pump is used, conventionally the pump is powered using a mains supply as the primary supply. The mains supply will typically be used to power not only the pump, but also a pump controller associated with the pump, which pump controller may be programmed to provide individualized delivery of the medical fluids from the container or bag to the patient. For example, the pump controller may be programmed to control the pump to provide a particular flow rate of the fluid.

It is also typically the case that a battery power supply is provided to power the pump and pump controller for a limited period of time. The battery power supply may be included to limit the possibility that a failure of the mains supply will result in an interruption of the delivery of fluids to the patient. The battery power supply may also be included to permit the pump and pump controller to be moved with the patient, during which time it may be impossible or impractical to connect the pump and pump controller to the mains supply, for example, patient transport for test procedures, bathroom visits, or prescribed ambulation to enhance recovery. It is frequently the case that patient transport of critical patients requires a very high assurance of battery operation duration, due to the life sustaining nature of patient infusions. Failure to meet battery operation duration in these situations may lead to life threatening situations, as can be observed in the FDA Manufacturer and User Facility Device Experience ("MAUDE") database.

Because it is expected that the battery power supply will only have to power the pump and pump controller for a limited period of time before the pump and pump controller are again coupled to the mains supply, these battery power supplies typically include one or more rechargeable batteries. When the pump and pump controller are again coupled to the mains supply, a charger can be activated to charge the batteries back to their full charge. One advantage of using rechargeable batteries is that it is not necessary for the healthcare provider to change the batteries after every discharge cycle so that the battery power supply is at full charge capacity for a subsequent discharge cycle.

While rechargeable batteries have a longer standby life than traditional, non-rechargeable batteries, rechargeable batteries do have an expected operational life, which may be estimated in terms of years and/or numbers of charge/discharge cycles. Eventually, the rechargeable batteries will need to be replaced. In addition, over the operational life of the rechargeable battery, the charge capacity of the battery will decrease.

As set forth in greater detail below, the present disclosure sets forth an improved assembly embodying advantageous alternatives to the conventional devices and methods discussed above. In particular, the present disclosure addresses the significant unmet need in the area of battery management for portable devices delivering critical therapies.

SUMMARY

According to an aspect of the present disclosure, a battery management system is provided for one or more batteries that are coupleable to a healthcare delivery system, the one or more batteries coupled to the healthcare delivery system when the healthcare delivery system is not coupled to an alternate power supply. The system includes a display unit, and a controller coupled to the display unit and programmed to determine when the healthcare delivery system is coupled to the one or more batteries, to control the display unit to display an initial number corresponding to a time remaining on battery (TROB) when the healthcare delivery system is coupled to the one or more batteries, to determine if the TROB is within a reserve range extending up to a reserve range maximum, the reserve range maximum being less than a maximum TROB, to change the TROB according to an operational state of the healthcare delivery system if the TROB is greater than the reserve range maximum, and to decrease the TROB without regard for the operational state of the healthcare delivery system if the TROB is less than the reserve range maximum.

According to another aspect of the present disclosure, a healthcare delivery system includes one or more batteries, a portable pump for use in intravenous delivery of medical fluids, the portable pump being coupleable the one or more batteries, a display unit, an input unit, and a pump controller coupled to the portable pump, the display unit and the input unit, the pump controller programmed to receive an input from the input unit and to control the portable pump to enter an operational state according to the input received. The healthcare delivery system also includes a display unit, and a controller coupled to the display unit and programmed to determine when the healthcare delivery system is coupled to the one or more batteries, to control the display unit to display an initial number corresponding to a time remaining on battery (TROB) when the healthcare delivery system is coupled to the one or more batteries, to determine if the TROB is within a reserve range extending up to a reserve range maximum, the reserve range maximum being less than a maximum TROB, to change the TROB according to an operational state of the healthcare delivery system if the TROB is greater than the reserve range maximum, and to decrease the TROB without regard for the operational state of the healthcare delivery system if the TROB is less than the reserve range maximum.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explic

DETAILED DESCRIPTION OF VARIOUS EMBODIMENTS

Although the following text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '___' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
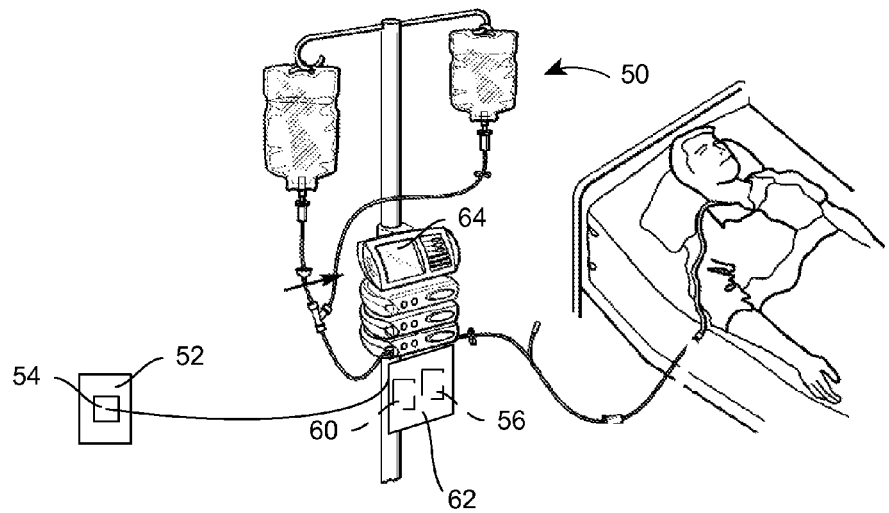
- FIG. 1 is a schematic view of a healthcare delivery system and a battery management system according to the present disclosure.

FIG. 1 illustrates a healthcare delivery system 50 according to the present disclosure. The healthcare delivery system 50 may be coupled to an AC mains supply 52 via a plug 54, or the healthcare delivery system 50 may be coupled to one or more batteries 56. For example, the healthcare delivery system 50 may be coupled to the mains supply 52 while the system 50 is stationary, for example in a patient's room. Alternatively, the healthcare delivery system 50 may be coupled to the one or more batteries 56 when the system 50 is being moved with the patient, or when a power source, such as the mains supply 52, is not otherwise available (i.e., when the system 50 is not coupled to an alternative power source).

The batteries 56 may be in the form of valve-regulated lead-acid batteries (such as #MD12020 available from Yuasa). As a consequence, unlike more recently designed batteries utilizing the Smart Battery specification, the state of charge and state of health of the batteries 56 is not readily determined by or available to the user of the batteries 56. The lack of information regarding the status of the batteries 56 makes calculation of remaining charge more complicated because information regarding the state of charge of the battery is not readily available. While the following system and method may have particular advantages when used with such batteries, it will be recognized that the system and method may still be advantageously used with other types of batteries as well.

Associated with the one or more batteries 56 is a battery management system 60. While the battery management system 60 is illustrated in FIG. 1 as being disposed in a common housing 62 with the batteries 56, this is simply one embodiment according to the present disclosure. For example, the battery management system 60 may be placed in a separate housing from the batteries 56, and then that subassembly may be connected or otherwise associated with the batteries 56.

Figure 2:
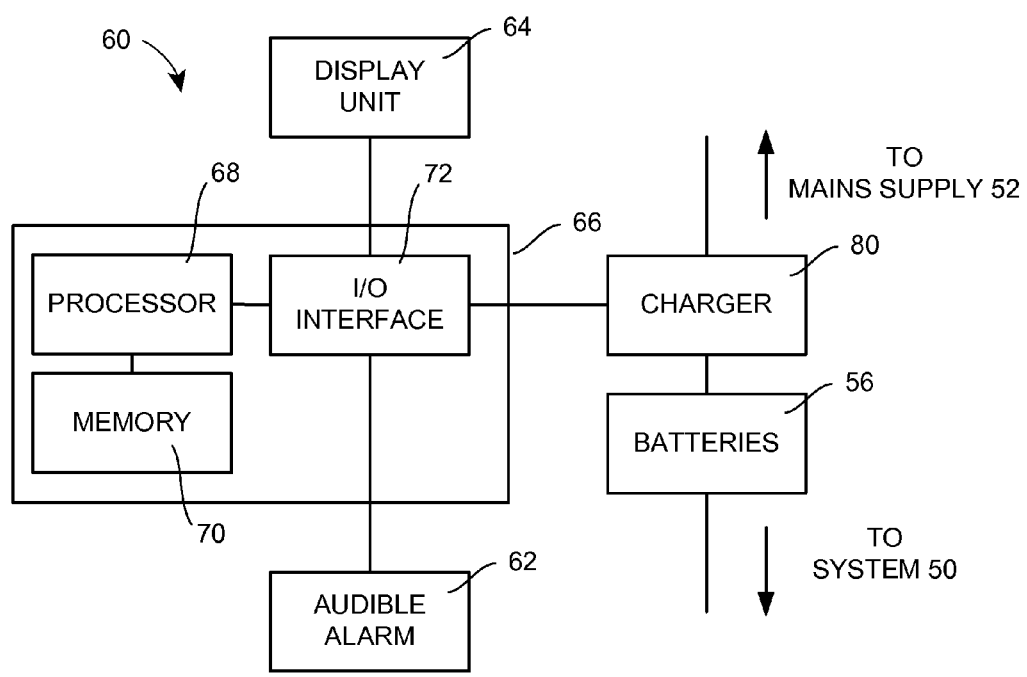
FIG. 2 is a block diagram of the battery management system of FIG. 1.

As illustrated in FIGS. 1 and 2, the battery management system 60 includes a display unit 64. In the illustrated embodiment, the display unit 64 may be utilized by the system 50 as well to display information to the healthcare provider other than information relating to the batteries 56 or the battery management system 60. However, according to other embodiments, the display unit 64 may be dedicated to the battery management system 60, and display only information relating to the battery management system 60.

As also illustrated in FIG. 2, the battery management system 60 includes a controller 66 coupled to the display unit 64. The controller 66 may include a processor 68, memory 70 and in input/output interface 72. The memory 70 may be in form of read-only memory (ROM) and random access memory (RAM). The ROM may take many different forms, including erasable programmable ROM (EPROM) and electrically erasable programmable ROM (EEPROM). In addition, for ease of illustration, the interface 72 has been represented as an input/output interface; it will be recognized that the interface 72 could be in the form of separate devices, one dedicated for input and the other dedicated for output.

The controller 66 is programmed to carry out a battery management method according to the present disclosure. In particular, the controller 66 may be programmed to carry out discharge and recharge of the batteries 56 for which only a limited amount of information regarding the state of charge and state of health of the batteries 56 may be available, although it will be recognized that it could be used for other situations as well. This method for discharge and recharge of the batteries 56 may operate according to a conservative modeling of the behavior of the batteries 56 and the healthcare delivery device 50 (in particular, its power consumption), although it may operate without conservative modeling as well. Further, this method may provide a value known herein as the time remaining on battery (TROB), which value is directly associated with the passage of time as determined by a clock associated with the controller 66 or clock function performed by the controller 66. Accordingly, the TROB may be referred to as deterministic, in that it uses a clock to determine the passage of time and associates the passage of time as measured by the clock with the ability of the battery to perform a particular operational state for a particular amount of time; this may be contrasted with existing systems that use a sensed parameter of the battery (such as voltage) to provide an estimate on battery life. Moreover, the method for discharge and recharge may seek to rigorously encourage user behavior so that the batteries 56 may be discharged and recharged in such a fashion that a high confidence (e.g., in excess of 90%, and according to certain embodiments, in excess of 95%) may be maintained when providing the user with a visual indication of the TROB in terms of units of time, such as hours, minutes or even seconds. Thus, it should be recognized that the TROB may be used in conjunction with the conservative modeling according to certain embodiments and separately from the conservative modeling according to other embodiments.

That is, according to conventional healthcare delivery devices incorporating battery management, an indicator may be provided to the user of the healthcare delivery device to indicate that one of three statuses exist, such as with green, yellow and red lights. These three states may be determined according to a sensed voltage level across the batteries when the healthcare delivery system 50 is being powered by the batteries. While the user may thus be able to differentiate a delivery device with fully charged batteries from a delivery device with partially or fully discharged batteries, such a system does not permit the user to determine with any degree of confidence the amount of time that the healthcare delivery device may be operated using the associated batteries. In fact, because the conventional method uses sensed voltages and because the voltages are dependent upon delivery rate for the associated healthcare delivery system (for example, a flow rate where the system includes a single or multi-channel pump), battery temperature, and the number of charge/discharge cycles already performed by the battery, the time when various alerts are provided may vary over the life of the battery. Under such conditions, it may not be possible to determine if the remaining power would permit movement of the patient and the associated healthcare delivery system (e.g., a pump and pump controller) from the patient's room to another area of the healthcare facility, e.g., for the administration of medical testing, during which time the healthcare delivery system would have to operate using the associated batteries.

To this end, the battery management system 60 (and in particular, the controller 66) is programmed to cause a display to provide a visual indication of the TROB on a display, such that the user may be able to compare the TROB with the time required to transport a patient, for example, and make a determination if the transport can be attempted with the existing equipment or if other equipment is required. Moreover, the battery management system 60 may use a method that causes the user to use the batteries in such a fashion as to avoid behavior that would stress the batteries 56 to a point wherein the TROB displayed to the user could not be relied upon to a high confidence.

According to certain embodiments of the present disclosure then, a controller 66 may be programmed to carry out a method that may include the following actions, although as explained below, the method may include other actions as well. In particular, the controller 66 may be programmed to determine when the healthcare delivery system is coupled to the one or more batteries, to control the display unit to display an initial number corresponding to a TROB when the healthcare delivery system is coupled to the one or more batteries, the TROB being determined according to a conservative modeling of the one or more batteries and the system, and to determine if the TROB is within a reserve range extending up to a reserve range maximum, the reserve range maximum being less than a maximum TROB. The controller 66 may also be programmed to change the TROB according to an operational state of the healthcare delivery system if the TROB is greater than the reserve range maximum, and to decrease the TROB without regard for the operational state of the healthcare delivery system if the TROB is less than the reserve range maximum.

By discharging the batteries according to a conservative modeling, in particular one that is conservative as to battery cycling (in numbers of cycles), temperature of discharge, and discharge voltage, the system 60 may provide for one or more of the following benefits. For example, a conservative modeling may assist in providing a TROB with high confidence. Moreover, by limiting the discharge voltage, possible damage to the batteries may be avoided, or at least limited, when compared with a system 60 that permits the batteries 56 to be discharged to the point permitted by conventional systems.

Moreover, the battery management system 60 may also include charger unit 80 coupled to the controller 66 and couplable to the one or more batteries 56. The controller 66 may be further programmed to activate the charger when the healthcare system is coupled to a mains voltage to charge the one or more batteries, and to increase the TROB either by a first increment or to the TROB maximum according to a recharge state of the one or more batteries.

By carrying out the charging (or recharging, as the two terms will be used interchangeably herein unless context suggests otherwise) that provides for a limited number of discrete increases in the TROB, the system 60 may provide for one or more of the following benefits. A limited number of increases, or givebacks, to TROB may facilitate associating a high confidence with each phase of the recharging process. By providing only a limited number of givebacks, the system may also limit the ability of the user to continuously discharge and recharge the batteries, because the user will be unable to accurately estimate the TROB except at the limited number of discrete givebacks permitted by the system 60. Thus, this method encourages the user not to use the batteries 56 in a charge/discharge operating range where the resulting charge currents during recharge are high. Instead, the user is encouraged to keep the healthcare delivery system coupled to the mains supply as often as possible. In fact, it is believed that when combined with the limitation of battery discharge voltage resulting from the use of conservative modeling, limiting the use of high charge currents may reduce battery damage by a significant amount, for example by 75%.

Figure 3:
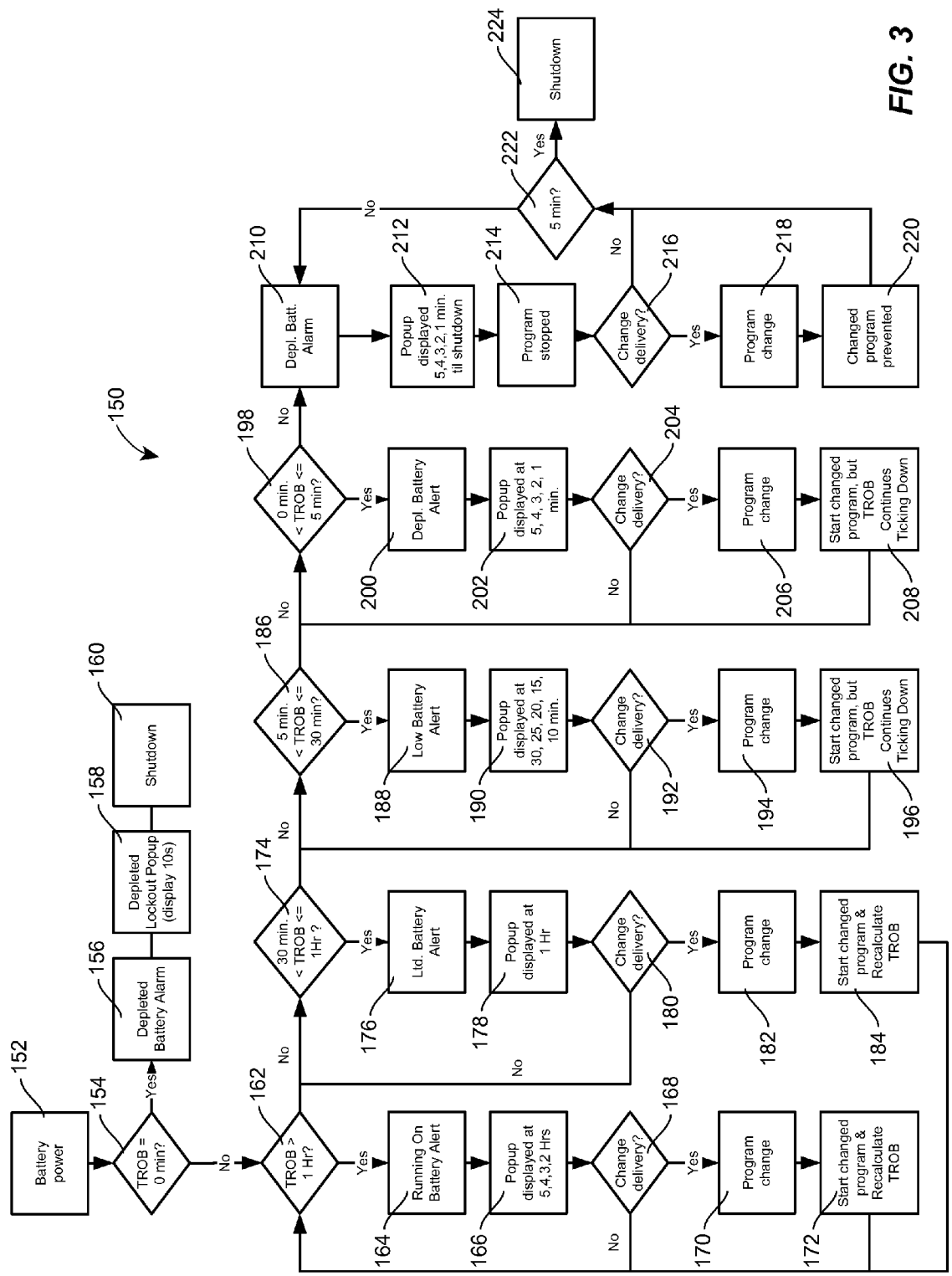
FIG. 3 is a flowchart of a method of managing discharge used by the battery management system according to FIG. 2.
Figure 4:
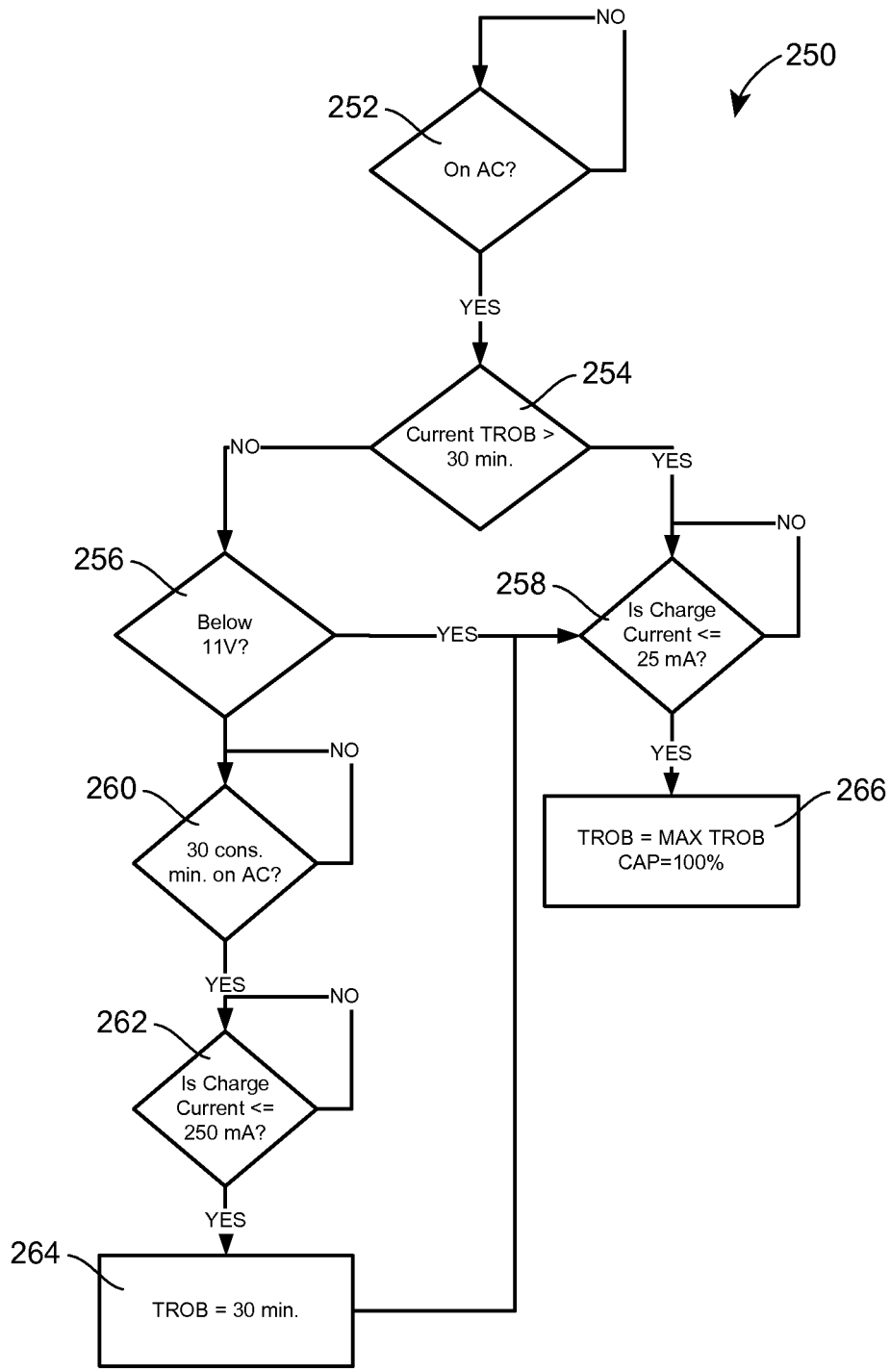
FIG. 4 is a block diagram of method of managing charging used by the battery management system according to FIG. 2.

Having thus explained the healthcare delivery system 50, the battery management system 60, their interaction, and the operation of the battery management system 60 in general terms, a more particularized discussion of the structure and operation of the illustrated embodiment of the systems 50, 60 is now described, with reference to FIGS. 1 and 2, and to FIGS. 3 and 4 as well. In particular, FIG. 3 illustrates an embodiment of a method 150 for managing discharge of the one or more batteries 56 associated with the system 50, while FIG. 4 illustrates an embodiment of a method 250 for managing charging the one or more batteries 56.

The method 150 begins at block 152 with the determination by the controller 66 that the healthcare delivery system 50 is coupled to the batteries 56. The controller 66 then makes an initial determination at block 154 if the TROB is equal to a minimum TROB. According to certain embodiments, the minimum TROB may be zero minutes. According to other embodiments, the minimum TROB may be set to a non-zero amount. However, if the determination is made at block 154 that the TROB is equal to the minimum TROB at block 154, the method proceeds to blocks 158 and 160, wherein the controller 66 activates an audible alarm 82 to notify the user that the TROB is equal to the minimum TROB, and controls the display 64 to display a visual alarm message to notify the use that the TROB is equal to the minimum TROB. The controller 66 may operate according to blocks 156 and 158 (which may be performed concurrently, rather than in series as illustrated) for a period of time, which may be set or determined in advance, for example 10 seconds. After the time period has elapsed, the controller 66 may cause the healthcare delivery system 50 to turn off or power down.

If the controller 66 determines instead that the TROB is not equal to the minimum TROB at block 154, the controller 66 may perform one or more determinations wherein the TROB is compared against one or more ranges or threshold values. Once the controller 66 has made the determination, the controller 66 may permit (or limit) the ability of changes of the system 50 between different operational states to cause a change in the TROB, may cause an audible or visual alert to be provided to the user, or even cause the system 50 to turn off or power down. While the embodiment of the method illustrated in FIG. 3 may provide four such range or threshold determinations, it will be appreciated that not every embodiment according to the present disclosure will include every such determination.

For example, the controller 66 operating according to the method 150 will permit changes in the operational states of the system 50 to affect the TROB if the TROB is greater than a maximum value set for a particular range of values, which may be referred to herein as the reserve range. Above this range (or above this threshold value, the reserve range maximum), the method 150 may make further determinations that dictate the nature of the information displayed or that affect other features of the operation of the system 50, but the battery management system 60 will change the TROB according to an operational state of the system 50. Similarly, within this range (or below the reserve range maximum), the method 150 may make further determinations that dictate the alerts provided or information displayed, but the battery management system 60 will decrease the TROB without regard for the operational state of the healthcare delivery system. However, while the illustrated embodiment may provide for multiple threshold determinations, a single threshold determination may be made instead with respect to the reserve range according to other embodiments.

According to certain embodiments of the system 60 according to the present disclosure, the TROB is determined with reference to one or more equations relating an effective battery capacity, a projected TROB (or PTROB), and the reserve range maximum with one or more tables that are the product of conservative modeling of the batteries 56 and the system 50. For example, the controller 66 may be programmed to determine an effective battery capacity (in percent) each second according to the following equation (Eqn. 1):

$$CAP = CAP - PCF*(1/3600), \text{ where}$$

CAP is the effective battery capacity (in excess of an amount required to provide the reserve range capacity); and PCF is an effective power consumption factor.

The effective capacity is initially set equal to 100% for a fully charged battery. The effective power consumption factor is determined based on conservative modeling for the batteries 56 and the healthcare delivery system 50. While the effective power consumption factor may be represented in a number of forms, the factor is provided in tabular form according to certain embodiments, with a different factor being determined for each of a limited number of delivery ranges. For example, where the system 50 is an infusion pump and pump controller, the following table may be used for a single channel pump:

| Single Channel Pump | | |
|---|---|---|
| Infusion Rate (ml/hr) | PTROB (hrs) | PCF (1/PTROB) |
| 801-1200 | 3.0 | 0.333 |
| 401-800 | 3.5 | 0.2857 |
| 101-400 | 4.0 | 0.25 |
| 0-100 | 4.5 | 0.222 |

Alternatively, the following table may be used for a multi-channel pump:

| Triple Channel Pump | | | | | | |
|---|---|---|---|---|---|---|
| Infusion Rate Range (ml/hr) | PTROB, 1 chan (hrs) | PTROB, 2 chans (hrs) | PTROB, 3 chans (hrs) | PCF, 1 chan (1/PTROB) | PCF, 2 chan (1/PTROB) | PCF, 3 chan (1/PTROB) |
| 801-1200 | 2.0 | 1.25 | 0.75 | 0.5 | 0.8 | 1.33 |
| 401-800 | 2.5 | 1.5 | 1 | 0.4 | 0.667 | 1 |
| 251-400 | 2.75 | 1.75 | 1.25 | 0.3636 | 0.571 | 0.8 |
| 0-250 | 3.0 | 2.0 | 1.5 | 0.333 | 0.5 | 0.667 |

In preparing this table, the modeling included the following assumptions regarding the operation of the batteries 56 and the system 50, wherein power consumption was maximized while battery capacity was minimized:

1. A conventionally low ambient temperature (15 C) was assumed to maximize consumption;
2. A conventionally low operating temperature for the battery (38 C) was assumed to minimize capacity;
3. A conventionally high number of charge/discharge cycles (e.g., 50-70) was assumed to minimize capacity;
4. The highest flow rate in each range was assumed to maximize consumption; and
5. The charge/discharge cycle with a final discharge voltage of 11V was assumed to minimize capacity.

In addition, the modeling assumed that adequate battery capacity would be reserved to provide for operation of the system 50 during the period of time previously referred to as the reserve range. For this period, additional assumptions were made to maximize consumption, including:

1. All channels (where multi-channel) operating at highest delivery (flow) rate; and
2. The display unit 64 operating at 50% backlight (normally assumed to be operating at 10% backlight).

Based on knowledge of the effective battery capacity (CAP), a current TROB may be determined using the following equation (Eqn. 2):

$$CTROB = PTROB*CAP + RRM, \text{ where}$$

CTROB is the current TROB;

PTROB is a projected TROB obtained from the tables provided above, according to the delivery rate (e.g., flow rate) then provided by the system 50;

CAP is the effective battery capacity; and

RRM is the reserve range maximum (in this case, 30 minutes).

Assuming then that the controller 66 determines at block 154 that the TROB is not equal to the minimum TROB (e.g., zero minutes), then the method 150 may continue to block 162, where the controller 66 determines if the TROB exceeds a first threshold amount. If the TROB exceeds this first threshold amount, then the method 150 proceeds to block 164, and the controller 66 causes the display unit 64 to display a visual warning to the user that the system 50 is operating on battery power. This may also be accompanied by an audible alert according to certain embodiments. The method 150 then proceeds to block 166 where the controller 66 causes the display unit 64 to provide a numerical, visual indication of the number of hours of battery life remaining. While this visual indicator may be decremented every second or minute, the controller 66 may instead determine that the indicator should only be changed only once per hour.

After performing block 166, the controller 66 programmed according to the method 150 may make a determination at block 168 as to whether the system 50 has received an input from the user representative of a decision to change the operational state of the system 50. For example, where the system 50 is a medical fluid delivery system including a pump and a pump controller, the user may enter a new infusion program with a higher or lower infusion rate than that presently provided by the system 50. If the determination is made at block 168 that the input has been received, the system 60 may receive data regarding the operational state change at block 170, and may change the TROB in keeping with the operational state change at block 172. That is, if a change to a higher flow rate is programmed, then the TROB may be decreased, while a change to a lower flow rate may result in an increase in TROB.

On the other hand, if the controller 66 determines at block 162 that the TROB is less than the first threshold amount (e.g., one hour), then the controller 66 determines at block 174 if the TROB is less than a second threshold amount, in particular the reserve range maximum. As one example, the reserve range maximum may be set to thirty minutes. If the controller determines that the TROB is not less than the reserve range maximum, the controller 66 continues to block 176.

At block 176, the controller 66 causes the display unit 64 to display a visual warning to the user that the system 50 has entered a range of limited battery power (e.g., TROB between one hour and thirty minutes). This may also be accompanied by an audible alert according to certain embodiments. The method 150 then proceeds to block 178 where the controller 66 causes the display unit 64 to provide a numerical, visual indication of the number of hours of battery life remaining (e.g., one hour). While this visual indicator may be decremented every second or minute, the controller 66 may instead determine that the indicator should only be displayed only once.

After performing block 178, the controller 66 programmed according to the method 150 may make a determination at block 180 as to whether the system 50 has received an input from the user representative of a decision to change the operational state of the system 50, similar to block 168. If the determination is made at block 180 that the input has been received, the system 60 may receive data regarding the operational state change at block 182, and may change the TROB in keeping with the operational state change at block 184.

Proceeding further, if the controller 66 determines at block 174 that the TROB is less than the reserve range maximum, then the method 150 continues to block 186, wherein a determination is made with reference to a third threshold amount (e.g., five minutes). This comparison is made to permit a phased progression of alerts to the user; according to alternative embodiments, it may not be desired or necessary to make the third threshold comparison, or the subsequent fourth comparison also illustrated. However, to afford the user a phased progression of alerts to limit the chances for surprise, multiple thresholds may be established.

If the controller determines at block 186 that the TROB is within the range of five to thirty minutes, then the method 150 continues to block 188, where the controller 66 causes the display unit 64 to display a visual warning to the user that the system 50 has entered a range of low battery power (e.g., TROB between five minutes and thirty minutes). This may also be accompanied by an audible alert according to certain embodiments. The method 150 then proceeds to block 190 where the controller 66 causes the display unit 64 to provide a numerical, visual indication of the number of minutes of battery life remaining (e.g., thirty minutes). While this visual indicator may be decremented every minute, the controller 66 may instead determine that the indicator should only be displayed in five minute increments.

After performing block 190, the controller 66 programmed according to the method 150 may make a determination at block 192 as to whether the system 50 has received an input from the user representative of a decision to change the operational state of the system 50, similar to block 168. If the determination is made at block 192 that the input has been received, the system 60 may still receive data regarding the operational state change at block 194. However, because the healthcare delivery system 50 is operating in the reserve range, the controller 66 will not change the TROB in keeping with the operational state change at block 196. Instead, the controller 66 continues to decrement the TROB without regard for the operational state of the healthcare delivery system. The controller 66 will continue to provide TROB to the user irrespective of the operational state of the healthcare delivery system 50 while the TROB is within the reserve range.

If the determination is made that the TROB is less than the third threshold at block 186, the method 150 continues to a determination with respect to a fourth threshold at block 198. At this point, the controller 66 determines if the TROB is greater than a reserve range minimum, which may be set to be zero minutes as illustrated. If the TROB is greater than the reserve range minimum, then the method 150 continues to block 200.

At block 200, the controller 66 causes the display unit 64 to display a visual warning to the user that the system 50 has entered a range of depleted battery (e.g., TROB between zero minutes and five minutes). This may also be accompanied by an audible alert according to certain embodiments. The method 150 then proceeds to block 202 where the controller 66 causes the display unit 64 to provide a numerical, visual indication of the number of minutes of battery life remaining (e.g., five minutes). While this visual indicator may be decremented in amounts less than a minute, such as in seconds, the controller 66 may instead determine that the indicator should only be displayed in one minute increments.

After performing block 202, the controller 66 programmed according to the method 150 may make a determination at block 204 as to whether the system 50 has received an input from the user representative of a decision to change the operational state of the system 50, similar to block 168. If the determination is made at block 192 that the input has been received, the system 60 may still receive data regarding the operational state change at block 206. However, because the healthcare delivery system 50 is operating in the reserve range, the controller 66 will not change the TROB in keeping with the operational state change at block 208. Instead, the controller 66 continues to decrement the TROB without regard for the operational state of the healthcare delivery system. The controller 66 will continue to provide TROB to the user irrespective of the operational state of the healthcare delivery system 50 while the TROB is within the reserve range.

The method 150 continues on to block 210 when the determination is made at block 198 that the reverse range minimum is met (e.g., the TROB is equal to zero minutes). In such a case, the controller 66 could simply begin to turn off or power down the healthcare delivery system 50. However, according to the illustrated embodiment, the controller 66 operating according to the method 150 may instead be programmed to provide one final five minute period before final power down of the healthcare delivery system 50.

Accordingly, the controller 66 would control the display unit 64 to display a visual warning to the user that the system 50 has entered a shutdown period (e.g., TROB has reached zero minutes). This may also be accompanied by an audible alert according to certain embodiments. The controller 66 may also cause the display unit 64 to provide a numerical, visual indication of the number of minutes of battery life remaining (e.g., five minutes). While this visual indicator may be decremented in amounts less than a minute, the controller 66 may instead determine that the indicator should only be displayed in one minute increments. The controller 66 may also stop any currently running infusions at block 214.

The controller 66 programmed according to the method 150 may then make a determination at block 216 as to whether the system 50 has received an input from the user representative of a decision to change the operational state of the system 50, similar to block 168. If the determination is made at block 216 that the input has been received, the system 60 may still receive data regarding the operational state change at block 218. However, because the healthcare delivery system 50 is operating in the shutdown range, the controller 66 prevents the system 50 from carrying out the programmed change. Instead, the controller 66 continues to decrement the TROB without regard for the operational state of the healthcare delivery system, and prohibits operation of the healthcare delivery system 50. The controller 66 will continue to provide TROB to the user irrespective of the operational state of the healthcare delivery system 50 while the TROB is within the shutdown range.

Once the controller 66 determines that the end of the shutdown range has been reached (e.g., five minutes have elapsed) at block 222, the controller 66 proceeds to shutdown the healthcare delivery system 50 at block 224.

Turning next to FIG. 4, the method 250 for charging the batteries 56 begins at block 252. At block 252, the controller 66 determines if the healthcare delivery system 50 is being powered using the mains supply. If the controller 66 determines that the healthcare delivery system 50 is not powered by the mains supply (e.g., the system 50 is coupled to the batteries 56, or the batteries have discharged and the system 50 is shutdown), then the controller 66 does not proceed with the method 250. However, if the controller 66 determines that the system 50 is coupled to the mains supply, then the controller 66 programmed according to the method 250 proceeds to block 254.

At block 254, the controller 66 determines if the TROB is greater than the reserve range maximum (e.g., thirty minutes). If the TROB is not greater than the reserve range maximum, then the method 250 continues to block 256; if it is, then the method 250 continues to block 258.

Continuing then to block 256, as a first precaution, the controller 66 determines at block 256 if the voltage of the batteries 56 has dropped below 11V. If it has, then the controller 66 will not change the TROB until a determination is made at block 258 that the battery is fully charged. Until then, even though the batteries 56 are still charging using the charger 80, the display unit 64 will not change in accordance with the state of recharge of the batteries 56. If the controller 66 determines at block 256 that the voltage 56 has not dropped below 11V, then the method 250 continues to block 260.

As a second precaution, the controller 66 determines at block 260 if the charger 80 has been coupled to the mains supply for more than a threshold period of continuous time, for example thirty consecutive minutes. If the charger 80 has not been coupled to the mains for more than thirty consecutive minutes, the method 250 does not continue to block 262, where a determination is made whether the charge current through the batteries 56 is below a first current threshold. In fact, if the charger 80 is decoupled from the mains supply before thirty consecutive minutes have elapsed, the controller 66 may restart the charging method 250 at block 252 when it detects that the charger 80 has be recoupled to the mains supply. When the controller 66 determines that the charger 80 has been coupled to the mains for more than thirty minutes, then the method proceeds to block 262.

At block 262, the controller 66 determines if the charge current is below a first current threshold. The first current threshold is representative of a first charge condition in the batteries 56. The method 250 does not continue until the charge current through the batteries 56 drops below the first current threshold. Once the charge current does drop below the first current threshold, the controller 56 controls the display unit 64 at block 264 to display one or more numerals representative of a first recharge amount, which may be equal to the reserve range maximum according to certain embodiments including the embodiment illustrated in FIG. 4. The method 250 then continues to block 258.

The controller 66 determines if the charge current is below a second current threshold at block 258. The second current threshold is representative of a second charge condition in the batteries 56. According to the illustrated embodiment, the second charge condition may correspond to the full charge condition of the batteries 56, although this need not be the case according to other embodiments.

Once the charge current drops below the second charge condition, then the method 250 continues to block 266, and the controller 56 controls the display unit 64 at block 266 to display one or more numerals representative of a second recharge amount, which may be equal to the full charge condition according to certain embodiments including the embodiment illustrated in FIG. 4. The controller 66 programmed according to the method 250 may then set the effective battery capacity to 100%.

The system 60 and the methods 150, 250 may provide such advantages as detailed above, and other advantages in addition.

What is claimed is:
1. A battery management system for one or more batteries coupleable to a healthcare delivery system, the one or more batteries coupled to the healthcare delivery system when the system is not coupled to an alternate power supply, the system comprising:
- a display unit;
- a controller coupled to the display unit and programmed:
  - to determine when the healthcare delivery system is coupled to the one or more batteries,
  - to control the display unit to display an initial number corresponding to a time remaining on battery (TROB) when the healthcare delivery system is coupled to the one or more batteries,
  - to determine if the TROB is within a reserve range extending up to a reserve range maximum, the reserve range maximum being less than a maximum TROB,
  - to change the TROB according to an operational state of the healthcare delivery system if the TROB is greater than the reserve range maximum, and
  - to decrease the TROB to count down the TROB without regard for the operational state of the healthcare delivery system if the TROB is less than the reserve range maximum.

2. The system according to claim 1, wherein the controller is programmed, if the TROB is greater than the reserve range maximum:
- to determine a first projected TROB according to a first operational state of the healthcare delivery system;
- to determine that the healthcare delivery system has changed from the first operational state to a second operational state; and
- to determine a second projected TROB according to the second operational state of the healthcare delivery system.

3. The system according to claim 2, wherein the controller is programmed to add the reserve range maximum to either the first projected TROB or the second projected TROB to determine the TROB.

4. The system according to claim 2, wherein the controller is programmed to determine the first projected TROB according to an effective battery capacity and a first battery life projection and to determine the second projected TROB according to the effective battery capacity and a second battery life projection.

5. The system according to claim 1, wherein the TROB is determined according to a conservative modeling of the one or more batteries and the healthcare system, if the TROB is greater than the reserve range maximum.

6. The system according to claim 5, wherein the TROB, the maximum TROB, and the reserve range estimate are based on modeled behavior of the one or more batteries and the healthcare delivery system.

7. The system according to claim 1, the system further comprising a charger unit couplable to the one or more batteries, the controller coupled to the charger unit and further programmed:
- to activate the charger when the healthcare system is coupled to a mains voltage to charge the one or more batteries, and
- to increase the TROB either by a first increment or to the TROB maximum according to a recharge state of the one or more batteries.

8. The system according to claim 7, the system further comprising a charger unit couplable to the one or more batteries, the controller coupled to the charger unit and further programmed:
- to activate the charger when the healthcare system is coupled to a mains voltage to charge the one or more batteries, and
- to increase the TROB by a first increment, by a second increment or to the TROB maximum according to a recharge state of the one or more batteries.

9. The system according to claim 7, wherein the recharge state is dependent upon a charge current through the one or more batteries.

10. The system according to claim 9, wherein the TROB is increased by the first increment according to a first recharge state associated with a first electric charge measurement, and the TROB is increased to the maximum TROB according to a second recharge state associated with a second charge current measurement, the second charge current measurement being less than the first charge current measurement.

11. The system according to claim 1, wherein the TROB is based on energy capacity for the one or more batteries dependent upon battery cycling and final discharge voltage of the one or more batteries, if the TROB is greater than the reserve range maximum.

12. The system according to claim 1, wherein the reserve range is based on energy capacity for the one or more batteries dependent upon battery cycling, battery temperature and final discharge voltage of the one or more batteries and an extreme operational duration for the healthcare delivery system.

13. A healthcare delivery system comprising:
- one or more batteries;
- a portable pump for use in intravenous delivery of medical fluids, the portable pump being coupleable the one or more batteries;
- a display unit;
- an input unit;
- a pump controller coupled to the portable pump, the display unit and the input unit, the pump controller programmed to receive an input from the input unit and to control the portable pump to enter an operational state according to the input received; and
- battery management system comprising a charger coupled to the one or more batteries and a controller coupled to the display unit, wherein the controller is programmed:
  - to determine when the portable pump is coupled to the one or more batteries,
  - to control the display unit to display an initial number corresponding to a TROB when the portable pump is coupled to the one or more batteries,
  - to determine if the TROB is within a reserve range extending up to a reserve range maximum, the reserve range maximum being less than a maximum TROB,
  - to change the TROB according to an operational state of the healthcare delivery system if the TROB is greater than the reserve range maximum,
  - to decrease the TROB to count down the TROB without regard for the operational state of the healthcare delivery system if the TROB is less than the reserve range maximum,
  - to activate the charger when the portable pump is coupled to the mains voltage to charge the one or more batteries, and
  - to increase the TROB either by a first increment or to the TROB maximum according to a recharge state of the one or more batteries.

14. The system according to claim 13, the system further comprising a charger unit couplable to the one or more batteries, the controller coupled to the charger unit and further programmed:
- to activate the charger when the healthcare system is coupled to a mains voltage to charge the one or more batteries, and to increase the TROB either by a first increment or to the TROB maximum according to a recharge state of the one or more batteries.

15. The system according to claim 14, wherein the recharge state is dependent upon a charge current through the one or more batteries.

16. The system according to claim 15, wherein the TROB is increased by the first increment according to a first recharge state associated with a first electric charge measurement, and the TROB is increased to the maximum TROB according to a second recharge state associated with a second charge current measurement, the second charge current measurement being less than the first charge current measurement.

17. The system according to claim 14, the system further comprising a charger unit couplable to the one or more batteries, the controller coupled to the charger unit and further programmed:
to activate the charger when the healthcare system is coupled to a mains voltage to charge the one or more batteries, and
to increase the TROB by a first increment, by a second increment or to the TROB maximum according to a recharge state of the one or more batteries.

18. The system according to claim 13, wherein the controller is programmed, if the TROB is greater than the reserve range maximum:
to determine a first projected TROB according to a first operational state of the healthcare delivery system;
to determine that the healthcare delivery system has changed from the first operational state to a second operational state; and
to determine a second projected TROB according to the second operational state of the healthcare delivery system.

19. The system according to claim 18, wherein the controller is programmed to add the reserve range maximum to either the first projected TROB or the second projected TROB to determine the TROB.

20. The system according to claim 18, wherein the controller is programmed to determine the first projected TROB according to an effective battery capacity and a first battery life projection and to determine the second projected TROB according to the effective battery capacity and a second battery life projection.

21. The system according to claim 13, wherein the TROB is determined according to a conservative modeling of the one or more batteries and the healthcare system, if the TROB is greater than the reserve range maximum.

22. The system according to claim 21, wherein the TROB, the maximum TROB, and the reserve range estimate are based on modeled behavior of the one or more batteries and the healthcare delivery system.

23. The system according to claim 13, wherein the TROB is based on energy capacity for the one or more batteries dependent upon battery cycling and final discharge voltage of the one or more batteries, if the TROB is greater than the reserve range maximum.

24. The system according to claim 13, wherein the reserve range is based on energy capacity for the one or more batteries dependent upon battery cycling, battery temperature and final discharge voltage of the one or more batteries and an extreme operational duration for the healthcare delivery system.

* * * * *